United States Patent [19]

Azzariti

[11] 4,438,099

[45] Mar. 20, 1984

[54] BURN TREATMENT

[76] Inventor: Vittorio Azzariti, Los Ficus 239-San Isidro, Lima 27, Peru

[21] Appl. No.: 328,815

[22] Filed: Dec. 9, 1981

[51] Int. Cl.$^3$ ............................................. A61K 35/70
[52] U.S. Cl. ........................................ 424/93; 424/45; 435/255; 435/921
[58] Field of Search ..................... 424/45, 93; 435/921, 435/255

[56] References Cited

PUBLICATIONS

*Chemical Abstracts,* vol. 77 (1972), p. 176, Abstract No. 98569e, Singh et al., "Incidence of Antibacterial Compounds in Fungi".

*Primary Examiner*—Thomas G. Wiseman
*Assistant Examiner*—Frederick W. Pepper
*Attorney, Agent, or Firm*—McAulay, Fields, Fisher, Goldstein & Nissen

[57] ABSTRACT

A spray of *Candida kruseii* is applied to the burned area of skin to allow for the healing of the burn and regeneration of the skin in the affected area. The *Candida kruseii* spray forms a crust over the affected area, allowing for a more rapid healing and skin regeneration in the affected area than is accomplished with prior burn control treatment. The *Candida kruseii* treatment is also effective with other open sores, such as varicose ulcers and decubitus ulcers.

3 Claims, No Drawings

BURN TREATMENT

FIELD OF THE INVENTION

Many treatments exist for the healing of skin burns. Obviously, two problems must be taken into account in such treatments, the healing of the open sore resulting from the damage, and the regeneration of a skin layer to cover this open sore. This second problem has been particularly acute, since there is an obvious desire that the regenerated skin match the surrounding skin, as closely as possible, in pigmentation.

While many treatments exist, all suffer from significant drawbacks. For example, with existing treatment, skin grafting is almost inevitable with third degree burns, and is frequently necessary even for second degree burns. Even then, the replacement skin is generally quite different in pigmentation from the surrounding skin, so that even though healing and cure are effective, severe cosmetic problems remain. While the physical problem may be solved, there is frequently no cure for the resulting psychological damage.

A treatment of relatively simple application, with a minimum of pain and a substantially decreased necessity for skin grafts, along with relatively rapid healing and skin regeneration, has long been sought. Additionally, such a treatment should provide for regeneration of skin which matches closely the pigmentation of the surrounding skin.

Such a treatment would also be desirable for other open skin sores, such as varicose ulcers and decubitus ulcers. The value of such a treatment is recognized not only for individual problems of burns, scalding, and open sores, but would be extremely valuable in cases of mass disasters, both natural and man-made.

The prior art on burn treatments has not been aware of *Candida kruseii*. Other species of Candida, such as *C. albicans* (Snelling et al *Canadian Medical Association Journal*, Sept. 9, 1978), *C. parapsilosis*) Brown et al, *Arch. Int. Med.*, December 1977) have been considered a "complication" during the burn treatment and open sores.

Thus, though *C. kruseii* has long been known, it has been viewed, at best, as a contaminant and, at worst, an infection producer among patients under severe immunosuppresive therapy. An adequate treatment for burn injuries has, at least for the same period of time, been sought. In accordance with the present invention the treatment of burn injuries, and treatments of other open skin sores, has been found to be successfully accomplished with *Candida kruseii* cultures.

BRIEF DESCRIPTION OF THE INVENTION

In accordance with the present invention, particularly in view of the prior art, it has unexpectedly been discovered that the use of a culture of *Candida kruseii* over a burned area results in more rapid healing and regeneration of skin than with any prior art treatment. It has been found that the application of the microorganism is easily accomplished by means of a spray, but it is not the only form of application. Equally good results have been obtained through the use of applicators, brushes, cotton swabs, etc., but spraying, which allows the direct and even spreading of the microorganism over the burn injury without further disturbing the tissues and avoiding contaminants for mishandling, is the preferred method of application. The spray of *Candida kruseii*, apparently in conjunction with the living and dead germs that adhere over the surface of the cutaneous burn, forms a polysaccharide crust over the surface of the burn. This crust results upon application of the spray of *Candida kruseii* culture over a period of, generally, three to four days following experience of the injury. The spraying is generally accomplished once or twice a day. If necessary, a third daily application can also be accomplished.

Over the several days of the application, the crust becomes thicker and stronger, hermetically sealing the burn surface and suppressing heat and pain. *Candida kruseii* blocks the survival of contaminant microorganisms over the burn. Because of the crust, the need for other coverings, such as gauze, cotton, or bandages, is eliminated.

The crust which forms must remain over the burn area until the crust spontaneously detaches. This spontaneous detachment generally begins in the sixth to eighth day after application and detachment is completed between the tenth and fourteenth day, depending upon the extent and depth of the burns. Following detachment of the crust, the skin appears normal, frequently smooth and pink. While there is a decrease in the pigmentation of the regenerated skin, in comparison to the adjacent, healthy skin, because of a primary depigmentation, the skin color recovers over a period of four to eight months and the difference between the regenerated skin and the skin in the unburned areas, is almost imperceptible.

Apparently, the polysaccharide crust which forms over the burn area acts as a substrate for the synthesis of new epidermal layers by the *Candida kruseii*.

The application of the *Candida kruseii* spray, resulting in the formation of a crust, and the healing of the underlying burn area with regeneration of skin has been proven in both animal and human treatments. The treatment is effective, not only for burn treatments, but for treatment of other open cutaneous sores, as well. Thus, it can be applied to varicose ulcers, and to decubitus ulcers. The healing is rapid. As compared with treatments of the prior art, less severe measures, such as skin grafting are normally unnecessary, and the results of the treatment are, generally, far more effective than those of the prior art.

DESCRIPTION OF THE PREFERRED EMBODIMENTS

In order to establish the efficacy of the sprayed *Candida kruseii* culture for treatment of burns, tests were first conducted on laboratory animals. Based upon the results obtained in Example 1, below, the culture in accordance with the present invention was employed on human subjects suffering from thermal burns.

EXAMPLE 1

Apparently healthy rabbits, with weights varying between two and four kilograms, were chosen for this example. The abdominal skin of 18 such rabbits were shaved, each animal anesthetized, and the abdominal skin burned by the application of gauze with water at 90° C. for a period of one minute. The animal was fixed according to the method of Guerra (1946) for the first five days.

During the test, the animals were fed with carrots and isotonic glucose solution, and the animals remained fixed. Of the 18 rabbits tested, the burns of four were deliberately infected with Pseudomona. They were clinically isolated, sensitive to gentamycin, and resistant to carbenicillin, ampicillin, dicloxacillin, and cephalosporin. A quantity of four of the rabbits were similarly infected with Staphylococcus epidermis. 17 of the rabbits were treated with a spray of the *Candida kruseii* culture, while one rabbit remained untreated as a reference. Treatment of the rabbits was repeated for the first three to four days, until there was the formation of a crust which was well adhered to the burned surface. Spontaneous detachment of the crust in uninfected rabbits began in about eight to ten days, leaving behind a perfectly healed skin, smooth and pink. The rabbits which were infected with Pseudomona showed a spontaneous detachment of the crust in ten to twelve days, with well healed skin. The same process was noted for the rabbits infected with the Staphylococcus epidermis. Each of the rabbits which had been treated with the culture of *Candida kruseii*, following the spontaneous detachment of the crust, showed regrowth of the hair in the days following detachment of the crust.

Of the rabbits which had been infected with the Pseudomona, treatment with gentamycin was counter productive in two of the cases, because of renal complications. Of those infected with the Staphylococcus epidermis, there was a slower recovery and additional treatment with penicillin and sulfas was necessary. There was no result in the Pseudomona infected rabbits on treatment with silver nitrate.

Subsequent to the animal testing referred to above, the spray of *Candida kruseii* was clinically tested on thermal burns at the Burns Center of the Children's Hospital of the Ministry of Health, Lima, Peru. While, as will be indicated below, the treatment was highly successful on children, it should not be considered that the method of the present invention is limited to the treatment of children. In fact, treatment of children for healing of burn wounds is more difficult than for adults, particularly with the spray of the *Candida kruseii* culture. To a great extent, this increased difficulty is due to the formation of the crust which promotes the healing in the *Candida kruseii* treatment in accordance with the present invention. It is extremely difficult with children, particularly the younger children involved in the studies to be detailed below, to render them immobile. Thus, problems with cracking of the crust, particularly near body joints, were much more frequent than they would have been had adults been similarly treated.

The clinical study involving the sprayed on *Candida kruseii* culture involved 35 children ranging in age from one to eight years, with a mean age of three years. These children suffered second and second and third degree burns caused by boiling liquids. The extent of the burns, according to the LUND scheme, varied from 5 to 32% of the body area, with a mean of 18.5%.

As indicated, the children suffered either second or second and third degree burns. Eighteen of the patients had second degree burns and 17 had both second and third degree burns. The second degree burns varied between 5 and 32% of the body surface, with a mean of 18.5%, while the third degree burns in the 17 patients involved, varied between 1% and 10%, with a mean of 5.5%.

The method established for treatment of the burn patients involves the following steps:

1. Cleaning of the burned and adjacent skin with normal saline solution and soap, eliminating blisters and devitalized tissue;
2. Reposition of circulatory volume by administration of plasma and Ringer Lactate (without potassium chloride), during the first 48 hours after the burn, the amount being selected in accordance with the needs of each case;
3. Spraying of a culture of *Candida kruseii* over the entire burned surface, following the cleaning; the spraying was repeated in daily applications during the first three to four days until a crust had formed covering the entire burned area, the crust remaining firmly adhered to the burned area. Where a rupture of the crust, or detachment of the crust from the skin occurred, additional sprays of the *Candida kruseii* culture were applied to maintain continuity of the crust;
4. Maintaining the treated burn area without other coverings or dressings until full consolidation of the crust; and
5. Application of antibiotics for the fifth through seventh days.

The application of the *Candida kruseii* culture spray over the burned surface produced a visible crust within 16 to 24 hours. The initial form of the adherent film was similar to collodion. This crust thickened and hardened, progressively, until appearing as a yellow-brownish crust in about three to four days. The warmth and pain normally produced by such a burn are mitigated as the crust covering forms. When the crust has become firmly adhered to the burned surface, the crust essentially seals the burn from the surrounding environment, inhibiting fluid loss and isolating the injured area from the environment.

The adherence of the crust to the burned area creates an anaerobic environment which, it is believed, plays an important role in some phases of the evolution and healing of the burn patients. These two aspects or phases involve the characteristics of the tissue regeneration which, in accordance with the present invention, involve an acceleration of epithelialization and the quality of the regenerated skin, which is typically normal and smooth in the second degree burn cases, and, secondly, the probable participation of anaerobiosis in the inhibition of bacterial development and local contamination.

The spontaneous detachment of the crust from the burn area began when the underlying skin was completely regenerated, which usually occurred between the fifth and sixth days, ending between the eighth and twelfth days. When the burns were of the skin of the face, the time for detachment of the crust was generally somewhat shorter, varying between six and nine days, in toto. When a larger amount of the body area was involved in second degree burns, as in those cases varying from 15 to 30%, or when there was deeper involvement, there was generally a delay in detachment of the crust and skin regeneration. Frequently, in such cases, detachment did not occur until the 15th to 18th day.

Of the 35 burn patients treated, 23, or 65.7%, had no local infection. The other 12 had local infections caused, in 11 cases, by *Staphylococcus albus*, either alone or associated, in two cases, with Pseudomona, in one case with proteus, and in one case with klebsiella. The other case of local infection was due, exclusively, to proteus.

The majority of the local infections developed late, specifically, between the seventh and ninth days. In some cases, the infections corresponded to infections suffered by patients in adjoining beds.

In some of the patients who suffered from local infections, additional treatments were administered in conjunction with the Candida kruseii culture spray. In seven of the cases, the Candida kruseii was complemented with gelonet, while an 0.5% solution of silver nitrate was administered to two.

In the second degree burn cases, when there was no local infection, healing and tissue regeneration occurred between the sixth and 15th day, with a mean time of 11.1 days. This was true in 23 cases. In the other 12 cases, where there was some local infection, the healing time was between 8 and 24 days. The mean healing time for all second degree burns, whether with or without local infection, was 12.2 days. By comparison, a mean healing time of 18 days is required in second degree burn cases, where there are no complications, when the burns are treated with an 0.5% solution of silver nitrate. This mean time of 18 days is experienced at the same hospital where the presently reported testing was carried out.

Of the 17 patients treated who had experienced third degree burns, a cure was effected in 8 cases employing only the spray of the Candida kruseii culture, without the need for skin grafts. In the other nine cases, skin grafts were required. The extension of body surface involvement in these 17 patients was a mean of 2.5% in the group not requiring skin grafts, and 4.9% in the group which did require skin grafts.

No local infection was experienced by 11 of the 17 patients with third degree burns, while there was a late local infection with 6 of the patients. Five of these had exclusively Staphylococcus albus, while one had both Staphylococcus albus and Pseudomona. The mean time for healing and regeneration of the uninfected third degree burn cases was 18.8 days for those which did not require a skin graft, and 30 days for those where grafting was necessary. In the 6 patients with local infection, the mean time for healing was 32 days for those where skin grafting was not required, and 57 days for those requiring skin grafts.

In some cases, healing times were longer than might otherwise have been expected because of other diseases being experienced within the hospital where the treatment was carried out. This was particularly true where grafting in the third degree burn cases was delayed and the complications were related to epidemics within the hospital.

The number of burn patients included within the survey was 35. Information relating to 34 of those patients is found, below, in Table 1:

TABLE 1

| | | \multicolumn{2}{c}{BURNED BODY AREA} | DAYS OF CAN- | LOCAL INFECTION | | |
|---|---|---|---|---|---|---|---|
| NUMBER OF PATIENT (Example) | AGE OF PATIENT | 2° Degree | 3° Degree | DIDA KRUSEII SPRAY APPLICATION | OR INTERCURRENT DISEASE DAY - TYPE | COMPLEMENTARY TREATMENT DAY - TYPE | CUTANEOUS REGENERATION DAY |
| 2[1] | 2 y | 9% | 3% | 1-4 | | | 12 |
| 3[2] | 1 y | 18% | 2% | 1-4 | | | 6 |
| 4 | 2 y 8 m | | 1-3 | | | 9 | |
| 5[3] | 2 y 5 m | 8% | 2% | 1-4 | | | 10 |
| 6 | 1 y 8 m | 12% | | 1-3 | | | 9 |
| 7[4] | 5 y | 12% | 8% | 1-5 | | | 12 |
| 8 | 5 y | 20% | | 1-7 | 8 Staphy. | 8 Gel. Fur. | 17 |
| 9 | 2 y | 32% | | 1-10 | 6 Staphy. Ps. | 10 Solv. Nitr. | 23 |
| 10[5] | 5 y | 14% | 1% | 1-5 | 7 Staphy. | | 20 |
| 11[6] | 3 y | 18% | 2% | 1-10 | 8 Sta. Kleb. | 8 Solv. Nitr. | 15 |
| 12 | 1 y 4 m | 10% | | 1-4 | | | 8 |
| 13[7] | 2 y 2 m | 8% | 2% | 1-4 | | | 13 |
| 14[8] | 1 y 6 m | 10% | 2% | 1-4 | 2 Common Cold | | 15 |
| 15 | 2 y | 18% | | 1-4 | | | 12 |
| 16[9] | 5 y | 19% | 2% | 1-4 | 8 Sta. Prot. | | 13 |
| 17 | 4 y | 14% | | 1-4 | | | 10 |
| 18 | 1 y 8 m | 10% | | 1-5 | | | 13 |
| 19[10] | 3 y | 15% | 3% | 1-5 | 17 Chickenpox | | 12 |
| 20[11] | 2 y | 12% | 5% | 1-5 | | | 13 |
| 21 | 4 y | 9% | 4% | 1-7 | 9 Staphy. | 10 Gel. Fur. | 14 |
| 22[12] | 3 y | 16% | 2% | 1-9 | 20 Chickenpox | | 12 |
| 23[13] | 6 y | 15% | | 1-6 | 6 Staphy. | | 57 |
| 24 | 3 y | 10% | | 1-4 | | | 10 |
| 25[14] | 8 y | 7% | 7% | 1-5 | 8 Staphy. 10 Typhoid 35 Scabies | 8 Gel. Fur. | 8 |
| 26 | 1 y 7 m | 25% | | 1-6 | | | 1 |
| 27 | 4 y 2 m | 12% | | 1-4 | | | 9 |
| 28 | 2 y | 13% | | 1-5 | 5 Staphy. | 5 Gel. Fur. | 14 |
| 29 | 5 y | 10% | | 1-7 | 7 Proteus | 7 Gel. Fur. | 24 |
| 30 | 1 y 4 m | 12% | | 1-4 | | | 8 |
| 31[15] | 5 y 8 m | 11% | | 1-5 | | | 10 |
| 32[16] | 4 y 3 m | 5% | 10% | 1-5 | 5 Staphy. Ps. | 5 Gel. Fur. | 10 |
| 33[17] | 4 y | 13% | | 1-6 | 8 Staphy. | 8 Gel. Fur. | 13 |
| 34[18] | 2 y | 9% | 6% | 1-5 | | | 9 |
| 35[19] | 1 y 5 m | 10% | 2% | 1-3 | | | 12 |

KEY TO TABLE 1
Staphy.: Staphylococcus albus
PS: Pseudomona aeruginosa
Proteus: Proteus mirabilis
Kb.: Klebsiella
Gel. Fur.: Gelonet + Furacin
Silv. Nitr.: Silver Nitrate 0.5%
FOOTNOTES TO TABLE 1

TABLE 1-continued

TREATMENT OF BURN PATIENTS WITH *CANDIDA KRUSEII* SPRAY AND RESULTS

| NUMBER OF PATIENT (Example) | AGE OF PATIENT | BURNED BODY AREA | | DAYS OF *CAN-DIDA KRUSEII* SPRAY APPLICATION | LOCAL INFECTION OR INTERCURRENT DISEASE DAY - TYPE | COMPLEMENTARY TREATMENT DAY - TYPE | CUTANEOUS REGENERATION DAY |
|---|---|---|---|---|---|---|---|
| | | 2° Degree | 3° Degree | | | | |

[1] There were two applications of the *Candida kruseii* spray to seal crusts which were broken by scratching. The second degree areas healed on the 12th day, while the third degree areas healed on the 18th day.

[2] Due to scratching over the neck and scapula, healing in those areas was delayed until the 15th day.

[3] In the areas of the third degree burn, skin was grafted on the 20th day, with good results.

[4] Skin was grafted on the 17th day over the third degree burn areas, the grafts taking fully.

[5] Additional sprays of *Candida kruseii* were added after treatment with the penicillin and novobiocin. While 90% of the burned surface had epithelialized in 20 days, the remaining 10% required an additional 10 days, with the complete skin regeneration in 30 days.

[6] On the eighth day of treatment, there was fever and leucocytosis. The crusts detached with purulent secretion. The culture showed Klebsiella and Staphylococcus. Ultimate skin regeneration was accomplished on this patient in 40 days.

[7] The crusts detached from the second degree burn areas on the 13th day, with complete epitheliazation. The third degree area was grafted on the 20th day, and the graft took well.

[8] The complete epitheliazation of the second degree areas was accomplished in 15 days. The third degree areas epithelialized, without skin grafts, in 21 days.

[9] The second degree area showed crust detachment and complete epitheliazation on the 13th day. There was a skin graft over the third degree areas on day 45, the delay being due to Proteus infection. The third degree areas healed on day 62.

[10] There was complete epitheliazation of the second degree areas on the 12th day. The third degree burn areas healed, without skin graft, on the 20th day.

[11] There was complete epitheliazation in 80% of the burned areas, as indicated. Skin grafting took place on day 20, and took well, and there was complete healing.

[12] There was complete epitheliazation of 90% of the burned area in 12 days; the remainder of the burned area regenerated, without skin grafting, in 20 days.

[13] There was partial epitheliazation on the 14th day. Skin grafts were accomplished on the 18th, 30th, and 44th days, and the patient was discharged on the 57th day.

[14] There was complete cutaneous regeneration of the second degree areas in 14 days. Grafts over the third degree areas were delayed until the 60th day because of the various infections. The third degree burns were completely healed with the skin grafts, and the patient was discharged on the 75th day.

[15] There was satisfactory healing 0f 90% of the burned skin after 10 days. However, because of rupture of the crust on flexion, additional sprays were required for the left shoulder and axilla and curing in those areas was not completed until the 20th day.

[16] The areas of second degree burn were regenerated by the 10th day. Skin grafts were necessary on the third degree areas and were accomplished on the 18th day, with complete epitheliazation in the third degree areas on the 32nd day.

[17] There was good healing and epitheliazation of the burned area on the 13th day. While there was no apparent infection, a culture showed Staphylococcus contamination. The remainder of the burned area healed completely in 24 days.

[18] There was complete epitheliazation of the second degree burn areas in 9 days. The third degree areas were skin grafted on the 23rd day, the graft taking well.

[19] By the 12th day, 95% of the burned area showed epitheliazation. The third degree areas healed well, without graft, in 15 days.

EXAMPLE 36

Because of a failure of communication with the doctor involved, one patient, 1 year and 6 months old, who had received second degree burns over 5% of the body with hot water, was not treated immediately with the *Candida kruseii* spray in accordance with the present invention. Rather, the *Candida kruseii* spray was applied on the 7th, 8th, and 9th days. Crusts formed on the 9th day and began to detach on the 15th day, with complete detachment being realized on the 21st day, with total epitheliazation of the skin. There were no complications.

As can be seen from examples 2 through 36, a large number of patients, with a wide variety of burn areas, including both second and third degree burns, have been successfully treated with *Candida kruseii* sprays in accordance with the present invention. The absence of other infections substantially reduces the time required for complete epitheliazation of the skin. Even when cracking is experienced, because of flexion, the affected area can be retreated with the *Candida kruseii* spray to generate a new crust and accomplish, essentially, the same results as prior to the cracking of the crust. As will further be observed from the results set forth in examples 2 through 36, in many cases skin grafting is not even required in order to accomplish a complete curing and regeneration of the skin.

In each of the examples referred to above, numbers 2 through 36, the patient was also treated with various additional, standard medications, including penicillin, plasma, and Ringer Lactate. The burn areas were, generally, cleaned during application of the *Candida kruseii* spray.

Because of the observations made during treatment of burn patients, as set forth in examples 2 through 36 above, particularly the ability of the *Candida kruseii* spray to stimulate tissue regeneration, its possible use in other, related areas, was also investigated. It was found to be successful for the treatment of chronic ulcers, both decubitus and trophic, for the treatment of varicose ulcers, and for treatment in regeneration in graft donor areas.

The *Candida kruseii* culture employed in examples 1 through 36, above, is prepared by incubating a culture of the *Candida kruseii*, and placing the culture, with a diluent, into spray containers containing a propellant. The *Candida kruseii* is then applied directly to the burn area by spraying from these containers.

A method of producing the *Candida kruseii* culture, and the one employed in the foregoing examples, follows:

EXAMPLE 37

A culture medium was prepared as follows:

| Material | Amount |
|---|---|
| Tryptone | 10 gr |
| Magnesium Sulphate | 370 mg |
| Glucose Powder | 10 gr |
| Monopotassium Phosphate | 650 mg |

-continued

| Material | Amount |
|---|---|
| Potassium Chloride | 500 mg |
| Manganese Sulphate | 3 mg |
| Distilled Water csp | 1000 ml |

The medium described above was sterilized in an autoclave at a pressure of 15 pounds for 15 minutes, with a pH7. The *Candida kruseii* germ was placed in this medium and incubated at 37° C. for 18 hours. Continuous readings were made with a spectrophotometer, and when a transmittancy of 50–70% was reached, the culturing was complete and ready for production. The culture produced was a solution and formed a membrane, seen in the upper part of the culture, and a sediment. The sediment and upper membrane were discarded, by standard processing techniques, and the solution retained. A quantity of 1000 ml. of the solution was diluted to 2000 ml. with sterile culture medium. Sterile bottles were filled with a quantity of 32 gr. of the diluted solution and 23 gr. of Freon 114. The filling of the solution was accomplished in a sterile environment. The aerosol valve was then placed on the container and sealed, rendering the *Candida kruseii* spray ready for use as in Examples 1 through 36. The packaged product has been found to have a two year life expectancy.

In addition to the Tryptone glucose medium shown in example 37, along with necessary minerals, other culture media yield goods results. These include agar sabouraud, tryptone saccharose, oxytetracycline-glucose-agar, and potato glucose agar.

The potency of the *Candida kruseii* culture employed in accordance with the present invention was determined according to various tests. The tests, and results, are as follows:

| | |
|---|---|
| Latency phase | 6 hours |
| Logarithmic phase | 4 hours |
| Declination | negative at 24 hours |
| Stationary phase | 12 hours |
| Generation time | 17 minutes |
| Number of generations | 14 |
| Bio-mass production | 996 × 10$^9$ |
| Bio-mass production per liter of culture | 2 gr./liter |
| Cellular packs (sediment) in 24 liters of culture | 50 gr. |
| Cellular linings per 10 gr. of cellular packs | 1.2 gr. |
| Cellular membranes in each 10 gr. of cellular packs | 0.050 gr. |
| Soluble enzymatic fraction in each 10 gr. of cellular packs | 3 ml |

The *Candida kruseii* culture suspensions employed in the examples in accordance with the present invention were found to be free of toxicity and side effects. Oral and parenteral administration to rats and mice, in acute, subacute, and chronic toxicity tests, in doses four times those used in the treatment of the burns, have produced no local reactions nor any significant variations in biological parameters. The biological parameters considered were hematological, renal, hepatic, and neurological.

The *Candida kruseii*, itself, as employed in the suspension according to the present invention, has been characterized, as follows:

| | |
|---|---|
| Form | polymorph (ovoid, bacillary, cylindrical) |
| Cellular disposition | unicellular masses |
| Size | 7 to 10 microns |
| Mobility | superficial sliding |
| Gram stain | positive |
| Special stains | |
| Ziehl Nielsen | negative |
| Sabatucci | capsules present |
| Gray | flagelles negative |
| Derner | spores negative |
| Rovinow | cellular material not organized |
| Pérez-Zapata | cellular material not organized |
| Ljubinsky | metachromatic granules present |

The *Candida kruseii* grows well only in oxygen. There was found to be abundant growth in aerobiosis, but scarce growth in anaerobiosis. Further, the temperature for incubation is important. There was scarce growth of the *Candida kruseii* at 20° C., no significant growth at 45° C., but abundant growth at 35° to 37° C.

The biochemical behavior of the *Candida kruseii* suspension employed for burn treatment in accordance with the present invention was evaluated, with the following results:

| | |
|---|---|
| Hydrogen sulfide | negative |
| Oxidase | negative |
| Starch hydrolysis | negative |
| Gelatin liquefaction | negative |
| Indole production | negative |
| Methyl red | negative |
| Acetyl methyl carbinol | negative |
| Casein hydrolysis | negative |
| Urease | negative |
| Milk peptonization | negative |
| Milk coagulation | negative |
| Catalase | positive |
| Nitrite reduction | positive |

In the culturing and incubation of the *Candida kruseii* to form the suspension in accordance with the present invention, carbon sources are necessary. Those which have been found to be useful, positively, are glucose, ethanol, glycerol, and DL-lactic acid. There is doubtful utilization of maltose, xylose, sucrose, raffinose, arabinose, and succinic acid. There is a negative utilization of inositol, manitol, saccharose, galactose, lactose, dulcitol, and citrate.

The antibiotic sensibility of the suspension was also tested, with the following results:

| | | |
|---|---|---|
| Gentamycin | 20 mcg | resistant |
| Chloramphenisol | 30 mcg | resistant |
| Novobiocin | 30 mcg | resistant |
| Ampicillin | 30 mcs | resistant |
| Rifamicin | 30 mcg | resistant |
| Carbenicillin | 100 mcg | resistant |
| Erythromycin | 15 mcg | resistant |
| Cephalosporine | 25 mcg | resistant |
| Dicloxacillin | 10 mcg | resistant |
| Aminosidine | 30 mcg | slight sensibility |

Further work toward the identification of the *Candida kruseii* was accomplished by obtaining of cellular packages from the suspension employed for burn treatment. Sediment from 24 liters of culture of each stock was washed and prepared according to the method of Strominger et al, obtaining approximately 50 grams of humid cellular package. The cellular package was washed, dried, and disintegrated according to the procedure of Caballero, Pacheco, and Palti (1971). The external envelopments were then separated by differential centrifugation and enzymatic treatment, according to the method of Rawun and Sieglin (1970). The sediment of cellular envelopments was treated according to the procedures of Braun and Rehn (1969) and of Braun and Sieglin (1970) to separate and purify the cellular wall.

The purified cellular wall as obtained above in a quantity of 50 grams was used to obtain peptidoglican according to the method of Mandeistam (1962) to obtain 3 mg. This purified peptidoglican was hydrolyzed according to the method of Henning, Rehn, and Rawun (1972) and was subjected to bidimensional paper chromatography according to the method of Gray and Wilkinson (1965). The chromatographic analysis of amino acids and sugars in this hydrolyzate gave the following results:

| Alanine | positive |
|---|---|
| Glutamic acid | positive |
| Ornitine | positive |
| Lysine | positive |
| Glycine | positive |
| N—muramic | positive |
| N—acetyl glucosamine | positive |
| Meso-diaminopimelic acid | negative |
| Serine | negative |
| Arginine | negative |
| Threonine | negative |
| Aspartic acid | negative |
| Valine | negative |
| Leucine | negative |
| Isoleucine | negative |
| Tirosine | negative |
| Arabinose | negative |
| Galactose | negative |

From a quantity of 10 grams dry weight of the cellular package obtained from the suspension, DNA was isolated according to the method of Thach and Newburger (1972). After hydrolysis of the nucleotides, the guanine-cytosine content of the isolated DSA, in a mean of three determinations, was 62 mol percent. Further characterization of the Candida kruseii from the suspension employed for burn control treatment was accomplished, with the following classification:
Division: Eumicete,
Class: Deuteromicete,
Order: Monilial,
Family: Moniliacea,
Genus: Candida.

The Candida kruseii according to the present invention meets the standard definition of the material of Van Uden and Buckley, as follows:

"Growth in glucose-yeast extract-peptone water: After 3 days at 25° C. the cells are cylindrical and ovoid. The relative amounts of cylindrical and oval cells vary with the strains. Usually cylindrical cells predominate. The size of the cells is mostly $(3-5) \times (6-20)\mu$. Smaller and much longer cells may also occur. A thin powdery pellicle that creeps up against the glass wall is readily formed in most strains. Growth in glucose-yeast extract-peptone agar: After one month at 25° C. the streak culture is greyish-yellow, semi-dull or dull, soft, usually smooth with some wrinkling near the bottom of the tube, or with the entire surface wrinkled; Pseudomycelial fringes may depart in a lateral direction from the margin. DALMAU plate cultures on corn meal agar: Pseudomycelium consists of elongated slender cells in a tree-like arrangement; at the points of branching, verticils of blastospores and chains of blastospores occur more or less abundantly, depending on the strain. In some strains the Pseudohyphae are curved and blastospore formation is scarce."

The identification of the active material as Candida kruseii was also confirmed by the National Center for Disease Control, with the following results:

| Fermentation Pattern | |
|---|---|
| Glucose | positive |
| Galactose | negative |
| Lactose | negative |
| Maltose | negative |
| Raffinose | negative |
| Sucrose | negative |
| Trehalose | negative |
| Assimilation Pattern | |
| Glucose | positive |
| Cellobiose | negative |
| Dulcitol | negative |
| Galactose | negative |
| Inositol | negative |
| Lactose | negative |
| Maltose | negative |
| Melibiose | negative |
| Raffinose | negative |
| Sucrose | negative |
| Trehalose | negative |
| Xylose | negative |
| Potassium Nitrate | negative |

Thus, in accordance with the present invention, it has been found that the suspension of a culture of Candida kruseii is useful in treating burns in both animals and humans. A Candida kruseii spray is produced from a culture and is sprayed onto the wounded area over a period of several days. For best results, the application of the spray is commenced as soon as possible after the injury. Continuous applications of the spray result in a crust forming over the damaged area, healing taking place below this crust, and the crust acting as a substrate for skin regeneration. Further, the presence of the crust ameliorates the pain normally encountered with such injuries. This Candida kruseii spray is also useful in the treatment of other open sore skin damage, such as tropic and decubitus ulcers.

While specific examples of the invention have been shown and described, the invention should be considered as limited only by the appended claims.

I claim:
1. A method for treating burn wounds comprising:
(a) applying to said burn wound a spray of a culture of Candida Kruseii;
(b) continuing application of said spray of Candida Kruseii to said burn wound until a crust forms covering said burn wound;
(c) allowing healing of said burn wound and regeneration of skin beneath said crust; and
(d) allowing said crust to spontaneously detach from said burn wound.
2. The method of claim 1 wherein the spray application of said Candida kruseii culture is continued for at least 3 days.
3. The method of claim 1 wherein additional medicinals are applied for the treatment of local infections.

* * * * *